United States Patent [19]

Asscher et al.

[11] 4,057,579
[45] Nov. 8, 1977

[54] ADDUCTS OF OLEFINS AND TRICHLOROMETHANE PHOSPHONIC DICHLORIDE

[75] Inventors: Meir Asscher; Hadassa Rosin, both of Rehovot, Israel

[73] Assignee: Rhone-Progil, Paris, France

[21] Appl. No.: 529,556

[22] Filed: Dec. 4, 1974

Related U.S. Application Data

[63] Continuation of Ser. No. 235,384, March 16, 1972, abandoned.

[30] Foreign Application Priority Data

Mar. 17, 1971 Israel .................................. 36431

[51] Int. Cl.$^2$ .............................................. C07F 9/34
[52] U.S. Cl. .................................. 260/543 P; 260/464; 260/465 R; 260/465 G; 260/465.1; 260/465.7; 260/502.4 R; 560/229; 560/192
[58] Field of Search ................................. 260/543 P

[56] References Cited
FOREIGN PATENT DOCUMENTS 2,212,798   9/1972   Germany ..................... 260/543 P

*Primary Examiner*—Norman Morganstern

[57] ABSTRACT

Adducts of trichloromethane phosphonic dichloride and olefinically unsaturated compounds having the general formula

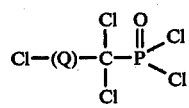

wherein Q designates:
a. $(CR''R'''—CRR')_n$
  wherein R and R', which may be the same or different, each designates
  H, alkyl or flourine;
  R" designates H, alkyl, aryl, substituted aryl, fluorine, chlorine, bromine, cyano, carbalkoxy, carboxy, acyloxy-methylene, acyloxy propylene, acetoxy, alkoxy, sulfonyl-alkyl or sulfonyl-aryl and R''' designates H, alkyl, fluorine, chlorine or bromine, or R and R" form together a ring system, and n is an integer of from 1 to about 500;
b. $(CH_2CR^{IV}=CR^VCH_2)_m$
  wherein $R^{IV}$ and $R^V$, which may be the same or different, each designates hydrogen, methyl or chlorine, and m is an integer of from 1 to about 200.

19 Claims, No Drawings

ADDUCTS OF OLEFINS AND TRICHLOROMETHANE PHOSPHONIC DICHLORIDE

This is a continuation of application Ser. No. 235,384, filed Mar. 16, 1972, now abandoned.

This invention relates to novel adducts of trichloromethane phosphonic dichloride, and to a process for their production. More particularly, it relates to the addition of trichloromethane phosphonic dichloride to olefinically mono- and polyunsaturated compounds and to the novel phosphonic dichlorides thus produced.

Trichloromethane phosphonic dichloride contains two chlorine atoms which are directly bound to phosphorus, and which are very reactive. It is an object of this invention to show that, unexpectedly, under free radical forming conditions, trichloromethane phosphonic dichloride reacts through chlorine of the trichloromethyl group, and not through chlorine bound to phosphorus. This could not have been foreseen, since other hetero-atom acid halides such as sulfonylchlorides are known to add readily onto a double bond through the chlorine atom which is bound to the hetero-atom.

The formed adducts, which may contain additional reactive functions on the carbon chain attached to phosphorus, depending on the olefins onto which trichloromethane phosphonic dichloride has been added, represent a novel class of phosphonyl halides. The direct introduction of a phosphonic dichloride function in a single step, by addition, was hitherto unknown.

The adducts may be used for a variety of purposes, including the synthesis of agricultural chemicals, flame-retarding additives, surface-active agents, extreme high pressure oil-additives, plasticizers and modifying and finishing agents for fibers and other polymers. Furthermore, the adducts obtained according to this invention may be dehydrochlorinated to give unsaturated compounds which are capable of polymerizing, either alone or with other monomers, yielding phosphorus and chlorine-containing polymers.

The present invention provides methods for the addition of trichloromethane phosphonic dichloride by which compounds of the formula $Cl(CR''R'''—CR'R)_nCCl_2P(O)Cl_2$ are produced, in which R and R' denote hydrogen, an alkyl group having 1–6 carbon atoms or fluorine, R'' may be hydrogen, alkyl having 1–12 carbon atoms, aryl, substituted aryl, fluorine, chlorine, bromine, cyano, carbalkoxy with an alkoxy group of 1–12 carbon atoms, carboxyl, acyloxy-methylene, acyloxy-propylene, acetoxy, alkyloxy having 1–6 carbon atoms, sulfonyl alkyl or sulfonyl aryl; and R''' may be hydrogen, alkyl having 1–6 carbon atoms, fluorine, chlorine or bromine. Furthermore R may be linked with R'' to form a ring. $n$ is an integer which may vary between 1 and about 500, depending on the particular method which is chosen for the interaction between trichloromethane phosphonic dichloride and the olefin, and on the olefin itself the chemical nature of which is defined by R, R', R'' and R'''.

When the reaction is directed towards the production of adducts where $n \geq 2$, the phosphonic dichloride may also react with a mixture of two or more olefins, provided that they conform to the definition of R, R', R'' and R'''.

Bis- and polyunsaturated compounds with unconjugated double bonds react like monoolefins, each double bond reacting independently of the other. Thus, novel adducts are obtained from polybutadiene, polyisoprene, or neoprene, which contains segments of the structure $+C(Cl)R—CH(CCl_2POCl_2)+$, in which R denotes either hydrogen, chlorine or methyl.

According to the processes which will be described in detail hereinafter, it is possible, by choosing the appropriate method, to control the value of $n$ of the general formula to a large degree.

Suitable olefins include ethylene, propylene, butene-1, butene-2, isobutene, octene-1, allyl acetate, allyl benzoate, diallyl phthalate, oleic acid and its methyl ester, vinyl acetate, vinyl butyrate, vinyl methyl ether, vinyl butyl ether, vinyl chloride, vinyl bromide, vinyl fluoride, vinylidene chloride, vinylidene fluoride, tetrafluoroethylene, trifluorochloroethylene, styrene, $\alpha$- or $\beta$-methyl styrene, p-chlorostyrene, p-nitrostyrene, divinyl benzene, p-vinylbenzoic acid, methyl acrylate, ethyl acrylate, butyl acrylate, acrylonitrile, acryloyl chloride, acrylamide, methacrylonitrile, crotonitrile, allyl cyanide, maleic anhydride, dimethyl maleate, diethyl fumarate, $\alpha$- and $\beta$-pinene, cyclohexene, cyclooctene, norbornene, norbornadiene, camphenyl acetate, p-tolyl vinylsulfone, 1,4-hexadiene, 1,5-hexadiene, polybutadiene, polyisoprene, neoprene or copolymers of butadiene, isoprene, dimethylbutadiene or chloroprene with other vinylic monomers such as acrylonitrile, acrylate esters, acrylic acid or styrene.

If the olefin is a conjugated diene, novel adducts of the general formula $Cl(CH_2CR=CR'CH_2)_nCCl_2POCl_2$ are produced, in which R and R' denote hydrogen, methyl and chlorine, and in which $n$ may vary between one and about 200, again depending on the method of reaction, which will be described in detail hereinafter. Suitable conjugated dienes include butadiene, isoprene, 2,3-dimethyl butadiene and chloroprene.

The olefins mentioned hereinbefore can be divided into two groups: those which polymerize and those which do not polymerize under free radical-producing conditions.

The second class of olefins give 1:1 adducts with trichloromethane phosphonic dichloride, i.e. products of the general formula $Cl(CR'''R''—CR'R)CCl_2POCl_2$ are obtained under all conditions which lead to the formation of free radicals. The reaction takes place when catalytic amounts of compounds, which decompose thermally into radicals, are added to a mixture of the olefin and trichloromethane phosphonic dichloride, and the mixture is subsequently heated to between 50° and 200°, preferably to between 80° and 150° C.

Alternatively, in the absence of free radical-producing compounds, the reactants can be irradiated with light of a wave length between 3600 and 2500 A, at a temperature between 0° and 150° C.

An inert solvent may be added, but it is only needed in order to assure a homogeneous solution with the catalyst.

Suitable compounds which produce radicals at an elevated temperature include azo-bis-isobutyronitrile, dibenzpinacol, ammonium persulfate, dibenzoyl peroxide, tertiary butyl perbenzoate, tertiary butyl hydroperoxide, cumene hydroperoxide, di-tertiary butyl peroxide and dilauroyl peroxide. The molar ratio between the olefin and the phosphonic dichloride may vary between 0.2 to 10, but is preferably close to one. Between 0.1 to 10 mole % of the catalyst, calculated on the phosphonic dichloride, is needed in order to secure reasonable conversions to adduct, but 1–5 mole % is sufficient in most cases. The reaction may be carried out either at atmospheric pressure or at pressures up to 300 atmospheres, depending on the olefin, the molar ratio between olefins and the phosphonic dichloride and the reaction temperature.

Internal olefins, when reacting under the conditions specified above, give exclusively 1:1 adducts. Olefins like propylene, butene-1 or allyl acetate give also 1:1 adduct, but low telomers are simultaneously formed. A higher proportion of telomers, together with 1:1 adduct is obtained from ethylene, the fluoroethylenes, chlorotrifluoroethylene, vinyl esters or vinyl ethers. For the telomers obtained in this case, $n$ varies from 2 to about 20, depending primarily on the molar ratio between the olefins and trichloromethane phosphonic dichloride and on the temperature of reaction.

If the conditions specified above are applied to the reaction between other polymerizable olefins and trichloromethane phosphonic dichloride, telomers are obtained for which $n$ of the general formula varies between 2 and about 500, depending among others on the nature of the olefin, the molar ratio between olefin and the phosphonic dichloride, and the reaction temperature. Other reaction parameters being equal, the lower range of $n$ is obtained from styrene, butadiene and the vinyl halides and the higher range from acrylate esters, acrylonitrile and the vinylidene halides. Mixtures of polymerizable olefins given telomers into which units of two or more monomers have been incorporated.

Another class of catalysts which brings about a reaction between olefins and trichloromethane phosphonic dichloride consists of iron metal or ferrous or ferric compounds. These compounds may be either simple salts such as sulfates, nitrates, acetates, chlorides, bromides or oxides, or coordination compounds such as iron phenanthroline or iron acetyl acetonate, or chloro- or bromoferrates in either valency state. In most cases, the preferred iron-containing catalyts are ferrous — or ferric chloride, either anhydrous or hydrated, the corresponding bromides, and the chloro- or bromoferrates which are derived from them.

The bromide-derived iron salts or complexes, or mixed chloride-bromide complexes perform as good as, but not better than, the more easily available chloride-containing iron salts or complexes. Especially preferred catalysts are the two- or three valency chloroferrates. They are easily prepared in situ by adding any chloride which is inert towards the reactants to an iron chloride containing solution, the most effective chlorides being those which have some solubility in the reaction medium.

Such chlorides include lithium chloride, ammonium chloride, methylammonium chloride, dimethyl-, trimethyl- and tetramethylammonium chloride, butyl- and tributylammonium chloride, laurylammonium chloride, dimethyldilaurylammonium chloride and the like. Again, the corresponding bromides perform as well, but offer no special advantage. The molar ratio of inert halide to iron halide may vary between 0.1 and 10, preferably between 0.5 and 6. The haloferrates formed in this way are more soluble in the reaction medium than ferric- or ferrous halide, and allow therefore a wider choice of solvents for the reaction.

A condition for a proper catalytic activity of the iron compounds is that they be at least partly soluble in the reaction medium. In the case of uncharged coordination compounds of iron, such as the acetylacetonates, there is no need for an additional solvent, but when iron salts and the iron halide complexes are used, such a solvent is frequently needed. It has to be inert towards the reactants and the catalyst, but has otherwise no restrictions. Suitable solvents include chloroform, methylene chloride, acetonitrile, propionitrile, dimethylformamide, dimethylacetamide, triethyl phosphate, diethylene glycol - diethylether, diethylsulfone and sulfolane.

Generally, a small amount of solvent is sufficient to bring about a homogeneous solution at the reaction temperature. Thus, a proportion of 0.1 to 1 of solvent with respect to the combined weight of the reactants is frequently sufficient.

The process of the invention can be carried out in more dilute solutions, but this offers no advantage. The olefin itself can, in certain cases, dissolve the iron compound catalyst, and then a solvent is not needed. This is the case for instance with unsaturated nitriles, and maleate esters. If iron metal is the sole catalyst, a solvent is needed which is capable of solvating iron ions. Such solvents include dimethyl formamide, dimethyl acetamide, acetonitrile and triethyl phosphate. In the presence of chloride ions, non-solvating solvents such as methylene chloride or chloroform may be used.

The reaction temperature, when using iron compounds as catalyst, may vary between 50° and 200° C, but 70°–150° C is the preferred range.

It is frequently advantageous to add a reducing agent to the iron compound. This particular mode of execution allows the process of the invention to be carried out at a lower temperature than in the absence of a reducing agent, thus ensuring a more selective reaction, giving produdts of an improved purity. Moreover, higher conversions of the reactants into the product are achieved.

Any convenient organic or inorganic reducing agent may be used, such as hydroquinone, benzaldehyde, acetone, acetophenone, isobutylaldehyde, benzoin, acetaldehyde, butyroin, 2,6-ditert. butyl-4-methylphenol, dihydroanthracene, dibenzpinacol, pyrogallol, 1- or 2-naphtol, iron metal, copper metal, stannous chloride, soluble sulfites and the like. The reducing agents may be used either alone or in admixture, in amounts varying between 0.1 to 10 moles with respect to the iron compound, preferably between 0.3 and 3 moles. They may be added at the start of the reaction or introduced gradually at reaction temperature. Sources of free radicals described in the first section, such as organic peroxides or azo-compounds have the same effect as reducing agents, if used in combination with the iron compound catalysts, in the molar ratios specified hereinbefore. In this particular combination, the catalytic effect of the iron compounds prevails, and the obtained products and their distribution are identical with those obtained for iron catalysis alone or in combination with a reducing agent.

A characteristic feature of the use of iron compounds as catalysts is a tendency towards formation of 1:1 adducts from trichloromethane phosphonic dichloride and olefins, in cases where catalysis by the conventional sources of free radicals leads to the formation of telomers. Many polymerizable olefins give a 1:1 adduct which may be accompanied by telomer. With monomers such as vinyl esters, vinylchloride, vinylbromide, vinyl ethers, butadiene, isoprene or styrene, the molar ratio between the reactants and other reaction conditions can be adjusted so as to yield either 1:1 adduct or telomers as the main product. With vinylidene chloride, acrylic esters, acrylic acid, acrylonitrile and the like, telomers always make up more than 50% of the reaction product.

Mixtures of vinylic monomers yield telomers in which two or more monomeric units are incorporated.

A third class of catalysts constitute cuprous or cupric compounds, or copper metal.

As in the case of iron compounds, coordination compounds as well as simple salts or oxides have a catalytic activity. The bromides and especially the chlorides are preferred. With copper compounds it is particularly advantageous to add an inert chloride of the same nature and in the same quantities as defined for iron and iron compounds. Its beneficial effect is manifest in improved yields, faster reactions, and the virtual absence of by-products.

The solvents which can be used for reactions catalyzed by copper compounds are the same as for iron and iron compounds. They are essential for the reaction only insofar as they bring about a homogeneous solution.

A reducing agent or a source of free radicals can be added in catalytic quantities, and has a distinct, though for certain olefins, a less pronounced effect that in the case of catalysis by iron compounds. The same reducing agents may be used as in the case of iron compounds. Again, the product distribution is not affected by these additives.

The reaction between olefins and trichloromethane phosphonic dichloride, when catalyzed by copper compounds, can be carried out at a temperature between 50° and 200° C, 70°–150° C being the preferred range.

The tendency to form 1:1 adducts from olefin and trichloromethane phosphonic dichloride is still much more pronounced for catalysis by copper compounds as compared to catalysis by iron or iron compounds. Thus, 1:1 adducts are always the main, and frequently the sole product from trichloromethane phosphonic dichloride and vinylic monomers or other olefins.

The following examples are given by way of illustration of the invention, but not by way of limitation. In the examples, all degrees are in centigrade.

EXAMPLE 1

Adducts of butene-1

5.6 g (0.1 mole)butene-1, 71 g (0.3 mole) trichloromethane phosphonic dichloride and 0.5 g tert. butyl perbenzoate were heated in 100 ml methylene chloride in a closed ampoule and in the absence of air, during 10 hours at 120°. After cooling, the ampoule was opened and its contents distilled. Unconverted trichloromethane phosphonic dichloride sublimed between 70° and 125° at 25 mm pressure. The continued distillation yielded 10.3 g 1.1,3-trichloropentane-1-phosponic dichloride, bp/0.05: 64°–66°. Found Cl: 61.3%. Calc. for $C_5H_8Cl_5OP$: 61.0%.

The adduct was quantitatively hydrolyzed to be the corresponding phosphonic acid monochloride, liberating 12.2% chlorine as chloride ions which was determined argentometrically. Calc: 12.2%. 5.8 g residue remained, consisting of telomers. Replacement of tert. butyl perbenzoate by ditert. butyl peroxide gave, after 10 hours heating at 125°, 13 g 1,1,3-trichloro-n-pentane-1-phosphonic dichloride.

EXAMPLE 2

Telomers of butadiene and of ethylacrylate 5.4 g (0.1 mole) butadiene, 11.8 g (0.05 mole) trichloromethane phosphonic dichloride, 10 ml dry methylene chloride and 0.1 g dibenzoyl peroxide were heated in a closed ampoule at 75° during 12 hours, after thorough degassing. After the reaction, the solution was run into rapidly stirred ice-cold isopropanol. The viscous mass which precipitated was dissolved again in methylene chloride, reprecipitated in isopropanol, and dried in vacuo.

In this way, 5.2 g telomer was obtained as a very viscous oil, with MW 3,950 and 5.2% chloride. It thus contains an average of 69 butadiene units per trichloromethane phosphonic dichloride unit.

The same reaction with ethylacrylate instead of butadiene yielded 10.2 g telomer, of MW 23,100 having 0.71% Cl and containing an average of 228 acrylate units per unit of telogen.

EXAMPLE 3a

Adducts of vinylchloride 6.25 g (0.1 mole) vinyl chloride, 23.6 g (0.1 mole) trichloromethane phosphonic dichloride, 540 mg (2 mmole) ferric chloride hexahydrate, 412 mg (3 mmole) triethylammonium chloride, and 424 mg (2 mmole) benzoin were heated in 30 ml acetonitrile in an ampoule at 100° during 15 hours. After opening of the ampoule, and evaporating unconverted vinyl chloride, the reaction product was diluted with methylene chloride, washed twice with ice-cold 1N aqueous hydrochloric acid and dried on calcium chloride. The solvent was distilled at atmospheric pressure, and unconverted phosphonic dichloride sublimed at 25 mm and 120°. The remainder was fractionated in vacuo, giving 8.3 g 1,1,3,3-tetrachloropropane-1-phosphonic dichloride, bp/0.1: 66°–67°; containing 70.3% Cl (Calc. for $C_3H_3Cl_6OP$: 71.0%).

Quantitative half-hydrolysis yielded 11.63% chloride ion. Calc: 11.88%. 6.5 g residue, a telomer containing an average of 3.5 vinylchloride units remained. Benzoin could be replaced by an equivalent amount of dibenzpinacol, with identical results. In the absence of any reducing agent, practically no adduct was obtained.

EXAMPLE 3b 11.8 g (0.05 mole) trichloromethane phosphonic dichloride, 6.25 g (0.1 mole) vinyl chloride, 100 mg (1 mmole) cuprous chloride and 63 mg (1.5 mmole) lithium chloride were heated in 10 ml acetonitrile in a sealed ampoule, under exclusion of air, during 20 hours at 125°. Subsequent treatment as in Example 3a afforded 11.5 g 1,1,3,3-tetrachloropropane-1-phosphonic dichloride, identical in all respects with the product obtained in Example 3a.

Cupric chloride for cuprous chloride gave identical results. The omission of lithium chloride caused the yield to decrease to 4.8 g adduct.

An equivalent amount of cupric acetylacetate yielded, after 20 hours at 125°, 3.9 g adduct. When 3 equivalents of lithium - or tetramethylammonium chloride were added, this yield rose to 8.3 g.

When the reactions were carried out in the presence of 134 mg (1 mmole) anhydrous cupric chloride, 206 mg (1.5 mmole) triethylammonium chloride and 366 mg (1 mmole) dibenzpinacol, 12.0 g adduct was obtained after 12 hours at 110°, showing an accelerating effect of the reducing agent.

EXAMPLE 4

Propylene adducts 11.8 g (0.05 mole) distilled trichloromethane phosphonic dichloride was dissolved in 10 ml acetonitrile, in the presence of 56 mg (1 mgr-at) iron powder. The mixture was transferred to a silver-lined autoclave of 100 ml capacity, purged with propylene, and pressurized with propylene under agitation until 4.2 g (0.1 mole) had dissolved. The autoclave was closed and heated at 30° under agitation during 6 hours. After cooling, unconverted propylene was released, and the contents of the autoclave filtered, and treated as in the previous example. Fractionation of the reaction mixture afforded 8.4 g 1,1,3-trichlorobutane-1-phosphonic dichloride, bp/0.04: 55°, and 1.2 g of the 2:1 telomer, 1,1,5-trichloro-3-methylhexane-1-phosphonic dichloride, bp/0.04: 99°–100°.

When the reaction was repeated with the combination of 56 mg (1 mgr-at) iron powder and 162 mg (1 mmole) anhydrous ferric chloride as the catalytic system, 6 hours heating at 30° afforded 11.3 g 1,1,3-trichlorobutane-1-phosphonic dichloride and 1.3 g 1,1,5-trichloro-3-methylhexane-1-phosphonic dichloride.

EXAMPLE 5

Adducts of ethylene 5.6 g (0.2 mole) ethylene, 23.6 g (0.1 mole) trichloromethane phosphonic dichloride, 162 mg (1 mmole) anhydrous ferric chloride and 366 mg (1 mmole) dibenzpinacol were heated in a 100 ml silver-lined autoclave in 40 ml dry methylene chloride at 120° during 14 hours. During this time the pressure fell from 500 to 220 psi. After cooling, the reaction product was extracted three times with ice-cold 1N aqueous hydrochloric acid after take-up in methylene chloride and dried on calcium chloride. Evaporation at atmospheric pressure at 50° left an oil which was distilled in vacuo, yielding 13.7 g 1,1,3-trichloropropane-1-phosphonic dichloride, bp/4: 105°–106°. Quantitative half-hydrolysis gave 13.4% chloride ion. Calc.: 13.4%.

5.3 g unconverted trichloromethane phosphonic dichloride was recovered and 4 g distillation residue remained. Continued distillation gave 2.5 g of the 2:1 telomer, 1,1,5-trichloropentane-1-phosphonic dichloride, bp/0.04: 70°–71°, and 0.5 g of the 3:1 telomer, 1,1,7-trichloroheptane-1-phosphonic dichloride, bp/0.04: 96°–98°. The same reaction, in the presence of 8.6 mg (2 mmole) lithium chloride yielded 19.2 g 1,1,3-trichloropropane-1-phosphonic dichloride. In the absence of dibenzpinacol, practically no reaction took place.

EXAMPLE 6

Adduct of Styrene 11.8 g (0.05 mole) trichloromethane phosphonic dichloride, 7.8 g (0.075 mole) styrene, 134 mg (1 mmole) anhydrous cupric chloride and 206 mg triethylammonium chloride were brought into solution by 5 ml acetonitrile, and heated in the absence of air in a sealed ampoule at 110° during 3.5 hours. After cooling and opening of the ampoule, the reaction mixture was subjected to fractionation in vacuo, through a short Vigreux column. 9.1 g pure 1:1 adduct, 1,1,3-trichloro-3-phenyl-propane-1-phosphonic dichloride was obtained bp/0.05: 121°. Found: Cl: 50.8, Calc. for $C_9H_8Cl_5OP$: 52.1%

The NMR spectrum was in agreement with the proposed structure. In the absence of triethylammonium chloride, the yield was 4.3 g.

EXAMPLE 7

Adduct of Acrylonitrile 11.8 g (0.05 mole) trichloromethane phosphonic dichloride, 134 mg (1 mmole) anhydrous cupric chloride and 206 mg (1.5 mmole) triethylammonium chloride were dissolved in 5.3 g (0.1 mole) dry acrylonitrile. The homogeneous solution was heated in the absence of air in a sealed ampoule, at 110°, for 15 hours. Fractionation as in the previous examples afforded 9.5 g pure 1:1 adduct, 1,1,3-trichloro-3-cyanopropane-1-phosphonic dichloride, bp/0.04: 90°–91°. Quantitative half-hydrolysis liberated 12.3% chloride ion; Calc.: 12.3%. The NMR spectrum agreed with the structure assigned to the 1:1 adduct.

EXAMPLE 8

Adducts of Butadiene 11.8 g (0.05 mole) trichloromethane phosphonic dichloride was dissolved in 10 ml dry methylene chloride, cooled, and a cold solution of 4 g butadiene in 10 ml methylene chloride, which also contained 134 mg (1 mmole) anhydrous cupric chloride and 206 mg (1.5 mmole) triethylammonium chloride, was added. The resulting homogeneous solution was heated in the absence of air, in a sealed ampoule, at 100° for 8 hours. After cooling, the reaction product was freed from solvent, and fractionated through a short Vigreux column. 9.6 g pure 1:1 adduct, 1,1,5-trichloro-pent-3-ene-1-phosphonic dichloride was obtained, bp/0.05: 92°–93°. Found: Cl: 61.3%, Calc. for $C_5H_6Cl_5OP$: 61.0%.

Quantitative half-hydrolysis liberated 12.3% chloride ion; Calc.: 12.25%. The NMR spectrum was in agreement with the structure assigned to the adduct. When cupric chloride was replaced by an equivalent quantity of ferric chloride, together with 1 mmole benzoin, 8 hours' heating at 100° yielded 5.2 g 1:1 adduct and 3.2 g 2:1 telomer $Cl(C_4H_6)_2CCl_2POCl_2$, bp/0.04; 125°–126°.

EXAMPLE 9

Adduct of Methylacrylate

To 11.8 g (0.05 mole) distilled trichloromethane phosphonic dichloride and 8.6 g (0.1 mole) methylacrylate was added a solution of 134 mg (1 mmole) anhydrous cupric chloride and 206 mg (1.5 mmole) triethylammonium chloride in 5 ml acetonitrile. The homogeneous solution was heated in the absence of air in a sealed ampoule at 125° for 15 hours. After cooling, the contents of the ampoule was subjected to distillation. 12.9 g 1:1 adduct, 1,1,3-trichloro-3-carbomethoxypropane-1-phosphonic dichloride was obtained, bp/0.04: 83°. Cl−(by half-hydrolysis): 11.23%. Calc. for $C_5H_6Cl_5O_2P$: 11.01%. In the absence of triethylammonium chloride, 3.7 g adduct was obtained.

EXAMPLE 10

Vinylidene Chloride Adducts 11.8 g (0.05 mole) distilled trichloromethane phosphonic dichloride, 134 mg (1 mmole) cupric chloride, 206 mg (1.5 mmole) triethylammonium chloride and 9.7 g (0.1 mole) vinylidene chloride were dissolved in 10 ml acetonitrile and heated in a sealed ampoule in the absence of air for 15 hours at 125°. After cooling, the reaction product was diluted with methylene chloride, once extracted with ice-cold 1N hydrochloric acid and twice with ice-water, and then dried on calcium chloride.

After evaporation of the solvent, the residue was subjected to distillation.

13.3 g 1,1,3,3,3-pentachloropropane-1-phosphonic dichloride was obtained, bp/0.04: 69°.

Chloride ion found on the basis of half-hydrolysis: 10.43%. (Calc.: 10.67%).

Continued distillation yielded 0.6 g of the 2:1 telomer, 1,1,3,3,5,5,5-heptachloropentane-1-phosphonic dichloride, bp/0.04: 118°–121°, chloride ion found: 9.17%. (Calc.: 8.24%).

EXAMPLE 11

Chloroprene Telomer 5.9 g (0.025 mole) trichloromethane phosphonic dichloride was heated at 70° for 15 hours in a sealed ampoule with 17.7 g (0.2 mole) chloroprene in 30 ml dry methylene chloride, in the presence of 136 mg azo-bis-isobutyronitrile. The mixture had been thoroughly degassed before sealing. After the reaction, the mixture was diluted with 100 ml methylene chloride and then slowly run into 1 liter ice-cold rapidly stirred isopropanol, the formed precipitate was collected, washed with cold isopropanol, and immediately dried in vacuo. It was dissolved again in 100 ml methylene chloride, re-precipitated in 1 liter cold isopropanol and dried in vacuo.

9.3 g of a polymer was thus obtained which had a molecular weight of 16400, and a chlorine content of 46.3%. It thus contained for every phosphonic dichloride end group, an average of 183 chloroprene units.

EXAMPLE 12

Polybutadiene Adduct 5.4 g all-cis polybutadiene was dissolved in 100 ml dry methylene chloride which also contained 11.8 g (0.05 mole) distilled trichloromethane phosphonic dichloride, 62 mg (1 mmole) anhydrous ferric chloride, 206 mg (1.5 mmole) triethylammonium chloride and 212 mg (1 mmole) benzoin. The viscous homogeneous solution was heated in a closed, glass-lined vessel under exclusion of air, for 5 hours at 100°. After cooling, the reaction mixture was run slowly into 1 liter ice-cold, rapidly stirred absolute isopropanol. The formed precipitate was filtered, washed well with cold isopropanol under exclusion of moisture, and dried in vacuo. 10.9 g of a polybutadiene-trichloromethane phosphonic dichloride adduct was obtained, which was film-forming, and soluble in methylene chloride, chloroform and diethylformamide, and which contained 46.8% Cl and 3.0% P. Films of this material were readily cross-linked by a solution of ethylene diamine in ethylacetate.

Examples 13–23

The adducts were prepared under the conditions specified in the table, and isolated as described in examples 3–10.

| Olefin | Molar Ratio Olefin:Telogen | Solvent (20 ml per 0.1 mole Telogen) | Catalyst (mole % On Telogen) | Chloride Added (mole per mole catalyst) | Reducing agent (moles per mole catalyst) | Hrs. | Temp. ° | PRODUCT $Cl(CR^{III}R^{II}-CRR^{I})$ R | R$^I$ | $CCl_2POCl_2$ R$^{II}$ | R$^{III}$ | Yield % Calc. on telogen | Boiling range (mm) | Found Cl* % | Calc. Cl⁻ % | Remarks |
|---|---|---|---|---|---|---|---|---|---|---|---|---|---|---|---|---|
| 13. Vinyl fluoride | 2 | $CHCl_3$ | $Fe(Acac)_3$(2) | — | DBP(1)* | 15 | 100 | H | H | H | F | 45 | 90–92 (25) | 12.3 | 12.6 | Without DBP, yield nil |
| 14. Vinylidene fluoride | 2 | $CHCl_3$ | $Cu(Acac)_2$(2) | — | DBP(2) | 15 | 125 | H | H | F | F | 63 | 105–106 (25) | 11.7 | 11.8 | Without DBP, yield 23% |
| 15. Vinyl bromide | 2 | $CHCl_2$ | $CuCl_2$(2) | TEAC****(2) | DPB(2) | 15 | 100 | H | H | H | Br | 78 | 66–67 (0.05) | 10.6 | 10.35 | Without DBP, yield 50% |
| 16. Chloro trifluoro ethylene | 2 | $CH_2Cl_2$ | $FeCl_3$(2) | TEAC(2) | Benzoin(2) | 15 | 100 | F | F | F | Cl | 43 | 50–52 (0.6) | 10.2 | 10.4 | |
| 17. cis-Butene-2 | 4 | DMF | $FeCl_3·6H_2O$(2) | $LiCl$(4) | Benzoin(2) | 15 | 100 | H | $CH_3$ | H | $CH_3$ | 80 | 60–61 (0.05) | 12.1 | 12.2 | Without benzoin, yield nil |
| 18. isobutene | 4 | DMF | $FeCl_3·6H_2O$(2) | $LiCl$(4) | Benzoin(2) | 15 | 100 | H | H | $CH_3$ | $CH_3$ | 85 | 60–62 (0.04) | 11.8 | 12.2 | '' |
| 19. Methyl-styrene | 2 | $CH_3CN$ | $CuCl_2$(2) | TEAC(4) | — | 5 | 110 | H | H | $C_6H_5$ | $CH_3$ | 71 | 128–129 (0.04) | 8.9 | 10.0 | Without TEAC, Yield 43% |
| 20. Butene-1 | 2 | $CH_3CN$ | $FeCl_3$(1) | — | Benzoin(2) | 10 | 90 | H | H | H | $C_2H_5$ | 55 | 60–62 (0.04) | 12.2 | 12.2 | Identified by gas Chromatography |
| 21. Butene-1 | 2 | $CH_3CN$ | $FeCl_2$(1) | TEAC(2) | — | 10 | 90 | H | H | H | $C_2H_5$ | 37 | '' | | | |
| 22. Butene-1 | 2 | $CH_3CN$ | $FeCl_3$(1) | TEAC(2) | — | 10 | 90 | N | N | N | $C_2H_5$ | 5 | '' | | | |
| 23. Butene-1 | 2 | $CH_3CN$ | $FeCl_3$(1) | — | Benzoin(2) | 10 | 90 | N | N | N | $C_2H_5$ | 85 | '' | | | |
| 24. Butene-1 | 2 | $CH_2Cl_2$ | — | — | — | 10 | 90 | H | H | H | $C_2H_5$ | 40 | — | 12.0 | 12.2 | Irradiated with U.V. light (3600–3000 R) |
| 25. Butene-1 | 2 | $CH_2Cl_2$ | — | — | — | 10 | 90 | — | — | — | — | — | — | nil | | |

*Chloride ion liberated after quantitative half — hydrolysis to phosphonic acid monochloride.
**Acac = Acetyl acetonate.
***DBP = Dibenzpinacol
****TEAC = Triethylammonium chloride.

The adducts were prepared under the conditions specified in the table, and isolated as described in examples 3–10

| Olefin | Molar Ratio Olefin:Telogen | Solvent (20 ml per 0.1 mole Telogen) | Catalyst (mole % On Telogen) | Chloride Added (mole per mole catalyst) | Reducing agent (moles per mole catalyst) | Hrs. | $Cl(CH_2CR^{IV}=CR^VCH_2)$ Temp. ° | R$^{IV}$ | $CCl_2POCl_2$ R$^V$ | Product Yield % calc. on telogen | Boiling Found range (min) | Cl⁻ % | Calc. % |
|---|---|---|---|---|---|---|---|---|---|---|---|---|---|
| 26. Isoprene | 2 | $CH_2Cl_2$ | $CuCl_2$(2) | TEAC | — | 5 | 110 | $CH_3$ | H | 88 | 105–106 (0.05) | 11.0 | 11.0 |
| 27. Chloropreno | 2 | $CH_2Cl_2$ | $CuCl_2$(2) | TEAC (1.5) | — | 5 | 110 | Cl | H | 90 | 113–115 (0.05) | 11.3 | 11.3 |
| 28. 2,3-Dimethyl butadiene | 2 | $CH_2Cl_2$ | $CuCl_2$(2) | TEAC (3) | — | 5 | 100 | $CH_3$ | $CH_3$ | 65 | 113–16 (0.05) | 10.5 | 11.2 |

We claim:
1. Compounds having the general formula

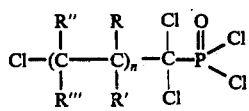

wherein R and R' may be the same or different and are each selected from the group consisting of hydrogen, $C_1$ to $C_6$ alkyl and fluorine; R" is selected from the group consisting of hydrogen, $C_1$ to $C_{12}$ alkyl, fluorine, bromine, chlorine, phenyl and substituted phenyl in which the substituent is selected from the group consisting of chlorine, a vinyl group, nitro and carboxy; R''' is selected from the group consisting of hydrogen, $C_1$ to $C_6$, alkyl fluorine, chlorine, bromine, or R and R" together define a ring selected from the group consisting of a cyclohexane ring, a cyclooctane ring, a norbornane ring, a norbornanone ring, a 2,6,6-trimethylbicyclo[3.1.1]heptane ring and a succinic anhydride ring; and n is an integer from 1 to about 500.

2. 1,1,3-trichloro-n-pentane-1-phosphonic dichloride.
3. 1,1,3,3-tetrachloropropane-1-phosphonic dichloride.
4. 1,1,3-trichloropropane-1-phosphonic chloride.
5. 1,1,3-trichloro-3-phenylpropane-1-phosphonic dichloride.
6. 1,1,3,3,3-pentachloropropane-1-phosphonic dichloride.
7. 1,1,3-trichloro-3-bromopropane-1-phosphonic dichloride.
8. 1,1,3-trichloro-3-fluoropropane-1-phosphonic dichloride.
9. 1,1,3-trichloro-3,3-difluoropropane-1-phosphonic dichloride.
10. 1,1,3-trichloro-n-butane-1-phosphonic dichloride.
11. 1,1,3-trichlorobutane-1-phosphonic dichloride.
12. 1,1,3-trichloro-3-methylbutane-1-phosphonic dichloride.
13. 1,1,3-trichloro-3-phenylbutane-1-phosphonic dichloride.
14. 1,1,3,3-tetrachloro-2,2,3-trifluoropropane-1-phosphonic dichloride.
15. 1,1,5-trichloropentane-1-phosphonic dichloride.
16. 1,1,3,3,5,5,5-heptachloropentane-1-phosphonic dichloride.
17. Cl$-(CH_2-CH_2)_n$-$CCl_2$-$POCl_2$, where $n$ is an integer of 1 to 50.
18. Cl$-(CHClCH_2)_n$-$CCl_2POCl_2$ in which $n = 2$ to 10.
19. 1,1,7-trichloroheptane-1-phosphonic dichloride.

UNITED STATES PATENT OFFICE
CERTIFICATE OF CORRECTION

Patent No. 4,057,579  Dated November 8, 1977

Inventor(s) MEIR ASSCHER and HADASSA ROSIN

It is certified that error appears in the above-identified patent and that said Letters Patent are hereby corrected as shown below:

IN THE SPECIFICATION

Columns 11 and 12 (Examples 13-23), in line "23. Butene-1" under the column entitled "PRODUCT" under column "R", delete "N" and insert therefor -- H --.

Columns 11 and 12 (Examples 13-23), in line "23. Butene-1" under the column entitled "PRODUCT" under column " R" ", delete "N" and insert -- H --.

Columns 11 and 12 (Examples 13-23), in line "24. Butene-1" under the column entitled "PRODUCT" under column " R' ", delete "N" and insert -- H --.

Columns 11 and 12 (Examples 13-23), in line "24. Butene-1" under the column entitled "PRODUCT" under column " R" ", delete "N" and insert -- H --.

Columns 11 and 12 (Examples 13-23), in line "26. Isoprene" in the last column entitled " C ", %
delete "17.7" and insert -- 11.7 --.

UNITED STATES PATENT OFFICE
CERTIFICATE OF CORRECTION

Patent No. 4,057,579　　　　　Dated November 8, 1977

Inventor(s) MEIR ASSCHER and HADASSA ROSIN

It is certified that error appears in the above-identified patent and that said Letters Patent are hereby corrected as shown below:

IN THE SPECIFICATION (continued)

Columns 11 and 12 (Examples 13-23), in line "28. 2,3-Dimethylbutadiene", under the column entitled "range", delete "113-16" and insert -- 113-116 --.
(min)

*Signed and Sealed this*

*Eighteenth* Day of *April 1978*

[SEAL]

Attest:

RUTH C. MASON　　　　　　　LUTRELLE F. PARKER
*Attesting Officer*　　　　*Acting Commissioner of Patents and Trademarks*